United States Patent
Staton et al.

(10) Patent No.: US 10,195,035 B1
(45) Date of Patent: Feb. 5, 2019

(54) RESPONSIVE BIOMECHANICAL IMPLANTS AND DEVICES

(71) Applicant: NEWTONOID TECHNOLOGIES, L.L.C., Liberty, MO (US)

(72) Inventors: Fielding B. Staton, Liberty, MO (US); David Strumpf, Columbia, MO (US)

(73) Assignee: Newtonoid Technologies, L.L.C., Liberty, MO (US)

(*) Notice: Subject to any disclaimer, the term of this patent is extended or adjusted under 35 U.S.C. 154(b) by 20 days.

(21) Appl. No.: 15/677,830

(22) Filed: Aug. 15, 2017

Related U.S. Application Data

(60) Provisional application No. 62/440,653, filed on Dec. 30, 2016.

(51) Int. Cl.
*A61F 2/30* (2006.01)
*A61F 2/38* (2006.01)
(Continued)

(52) U.S. Cl.
CPC ............ *A61F 2/30* (2013.01); *A61F 2/30721* (2013.01); *A61F 2/389* (2013.01); *A61F 2/3859* (2013.01); *A61F 2/604* (2013.01); *A61F 2/32* (2013.01); *A61F 2/442* (2013.01); *A61F 2/64* (2013.01); *A61F 2/6607* (2013.01); *A61F 2/72* (2013.01); *A61F 2/80* (2013.01); *A61F 2002/301* (2013.01); *A61F 2002/3057* (2013.01); *A61F 2002/3067* (2013.01); *A61F 2002/30079* (2013.01); *A61F 2002/30095* (2013.01); *A61F 2002/30098* (2013.01);
(Continued)

(58) Field of Classification Search
CPC .. A61F 2002/30563; A61F 2002/30565; A61F 2002/30573; A61F 2002/30558; A61F 2/30; A61F 2/32; A61B 17/88; A61B 17/8805; A61B 17/7097; A61B 17/8833; A61B 17/7095; A61B 17/7061; A61B 17/7094
See application file for complete search history.

(56) References Cited

U.S. PATENT DOCUMENTS 3,707,006 A * 12/1972 Bokros ................ A61C 8/0012
424/422
3,806,960 A * 4/1974 Weber ................ A61F 2/30771
623/22.14
(Continued)

OTHER PUBLICATIONS

PCT Application No. PCT/US17/68697, International Search Report and Written Opinion, dated Feb. 12, 2018, 7 pages.

*Primary Examiner* — Alvin Stewart
(74) *Attorney, Agent, or Firm* — Lathrop Gage L.L.P.

(57) ABSTRACT

The present disclosure includes joint replacement implants. The joint replacement implant allows for full articulation of the joint, while absorbing impact of the components during normal use that will reduce wear on the implant components and prolong life. The joint replacement implant may include a bone implantable component and a bearing component having an articulation surface that is sized and shaped to substantially mate with at least a portion of the bone implantable component and a damping mechanism that includes a contact member disposed at least primarily inside a cavity; a biasing member biasing the contact member toward an upper aperture of the cavity and means for capturing the contact member within the cavity.

24 Claims, 10 Drawing Sheets

(51) Int. Cl.
*A61F 2/60* (2006.01)
*A61F 2/32* (2006.01)
*A61F 2/44* (2006.01)
*A61F 2/50* (2006.01)
*A61F 2/64* (2006.01)
*A61F 2/66* (2006.01)
*A61F 2/68* (2006.01)
*A61F 2/48* (2006.01)
*A61F 2/72* (2006.01)
*A61F 2/80* (2006.01)
*A61F 2/78* (2006.01)

(52) U.S. Cl.
CPC ............... *A61F 2002/30105* (2013.01); *A61F 2002/30563* (2013.01); *A61F 2002/30565* (2013.01); *A61F 2002/30566* (2013.01); *A61F 2002/48* (2013.01); *A61F 2002/5004* (2013.01); *A61F 2002/6614* (2013.01); *A61F 2002/6863* (2013.01); *A61F 2002/7818* (2013.01)

(56) References Cited

U.S. PATENT DOCUMENTS

| | | | | |
|---|---|---|---|---|
| 4,813,961 A * | 3/1989 | Sostegni | A61F 2/34 | 623/22.14 |
| 4,822,369 A * | 4/1989 | Oueveau | A61F 2/32 | 623/22.14 |
| 5,181,926 A * | 1/1993 | Koch | A61F 2/30 | 623/22.14 |
| 5,197,987 A * | 3/1993 | Koch | A61F 2/38 | 623/20.28 |
| 5,201,881 A * | 4/1993 | Evans | A61F 2/34 | 623/20.28 |
| 5,358,525 A * | 10/1994 | Fox | A61F 2/30756 | 623/14.12 |
| 5,593,445 A * | 1/1997 | Waits | A61F 2/3099 | 623/23.39 |
| 5,735,905 A * | 4/1998 | Parr | A61F 2/3609 | 623/23.11 |
| 6,258,126 B1 * | 7/2001 | Colleran | A61F 2/38 | 623/20.29 |
| 6,607,560 B1 * | 8/2003 | Pfaff | A61F 2/30965 | 623/22.45 |
| 6,972,042 B2 | 12/2005 | Benson | | |
| 8,303,664 B1 * | 11/2012 | Burstein | A61F 2/30756 | 623/18.11 |
| 9,662,218 B2 * | 5/2017 | Grotz | A61F 2/3859 | |
| 9,808,345 B2 * | 11/2017 | Grotz | A61F 2/30721 | |
| 9,848,990 B2 * | 12/2017 | Winslow | A61F 2/4081 | |
| 2001/0051831 A1 * | 12/2001 | Subba Rao | A61F 2/3609 | 623/22.42 |
| 2002/0143402 A1 * | 10/2002 | Steinberg | A61F 2/30742 | 623/22.16 |
| 2003/0074077 A1 * | 4/2003 | Taylor | A61F 2/34 | 623/22.26 |
| 2004/0024460 A1 * | 2/2004 | Ferree | A61F 2/34 | 623/17.12 |
| 2004/0030398 A1 * | 2/2004 | Ferree | A61F 2/34 | 623/20.32 |
| 2004/0044410 A1 * | 3/2004 | Ferree | A61F 2/34 | 623/17.13 |
| 2004/0260396 A1 * | 12/2004 | Ferree | A61F 2/28 | 623/17.12 |
| 2005/0027364 A1 * | 2/2005 | Kim | A61F 2/4425 | 623/17.13 |
| 2005/0033437 A1 * | 2/2005 | Bao | A61F 2/442 | 623/17.15 |
| 2005/0038516 A1 * | 2/2005 | Spoonamore | A61F 2/4425 | 623/17.14 |
| 2005/0055101 A1 * | 3/2005 | Sifneos | A61F 2/389 | 623/20.32 |
| 2005/0171604 A1 * | 8/2005 | Michalow | A61F 2/38 | 623/14.12 |
| 2005/0202371 A1 * | 9/2005 | McGuire | A61C 8/00 | 433/201.1 |
| 2006/0064169 A1 * | 3/2006 | Ferree | A61F 2/32 | 623/17.12 |
| 2006/0241758 A1 * | 10/2006 | Peterman | A61B 17/562 | 623/17.11 |
| 2007/0100457 A1 * | 5/2007 | Hyde, Jr. | A61B 17/88 | 623/18.12 |
| 2007/0219640 A1 * | 9/2007 | Steinberg | A61F 2/32 | 623/22.12 |
| 2008/0103607 A1 * | 5/2008 | Krehl | A61F 2/389 | 623/39 |
| 2008/0288074 A1 * | 11/2008 | O'Neil | A61F 2/442 | 623/17.16 |
| 2008/0306609 A1 * | 12/2008 | Lee | A61B 17/72 | 623/23.58 |
| 2009/0005878 A1 * | 1/2009 | Tuke | A61F 2/34 | 623/22.24 |
| 2009/0024166 A1 * | 1/2009 | Carl | A61B 17/7064 | 606/247 |
| 2009/0093887 A1 * | 4/2009 | Walter | A61F 2/30721 | 623/22.11 |
| 2009/0234453 A1 * | 9/2009 | Steinberg | A61B 17/1617 | 623/16.11 |
| 2009/0248166 A1 * | 10/2009 | Linares | A61F 2/30771 | 623/18.11 |
| 2009/0259312 A1 * | 10/2009 | Shterling | A61F 2/38 | 623/14.12 |
| 2009/0259314 A1 * | 10/2009 | Linder-Ganz | A61F 2/3872 | 623/14.12 |
| 2010/0145451 A1 * | 6/2010 | Dee | A61F 2/30756 | 623/14.12 |
| 2010/0145464 A1 * | 6/2010 | Sidhom | A61F 2/30 | 623/18.12 |
| 2010/0241234 A1 * | 9/2010 | Linares | A61F 2/30 | 623/18.11 |
| 2011/0098823 A1 * | 4/2011 | Jukes | A61F 2/389 | 623/20.32 |
| 2011/0130844 A1 * | 6/2011 | Ratron | A61F 2/30756 | 623/23.42 |
| 2011/0190904 A1 * | 8/2011 | Lechmann | A61B 17/7208 | 623/23.61 |
| 2011/0257749 A1 * | 10/2011 | Fleischmann | A61F 2/38 | 623/17.16 |
| 2011/0257754 A1 * | 10/2011 | Fleischmann | A43B 1/0054 | 623/18.12 |
| 2012/0064288 A1 * | 3/2012 | Nakano | A61F 2/3662 | 428/117 |
| 2012/0116310 A1 * | 5/2012 | Forsell | A61B 17/1666 | 604/151 |
| 2012/0116523 A1 * | 5/2012 | Forsell | A61B 17/1666 | 623/18.11 |
| 2012/0221115 A1 * | 8/2012 | Komistek | A61F 2/32 | 623/22.15 |
| 2012/0277881 A1 * | 11/2012 | McShane | A61F 2/389 | 623/20.31 |
| 2012/0303130 A1 * | 11/2012 | Winslow | A61F 2/4081 | 623/19.12 |
| 2012/0323333 A1 * | 12/2012 | Metzger | A61F 2/389 | 623/20.32 |
| 2013/0030542 A1 * | 1/2013 | Grotz | A61B 17/0642 | 623/20.35 |
| 2013/0046388 A1 * | 2/2013 | Preuss | A61F 2/34 | 623/22.21 |
| 2013/0090737 A1 * | 4/2013 | Flaherty | A61F 2/30749 | 623/19.13 |
| 2013/0090740 A1 * | 4/2013 | Linares | A61F 2/4225 | 623/21.19 |
| 2014/0180424 A1 * | 6/2014 | Dickerson | A61F 2/3609 | 623/19.12 |
| 2014/0316526 A1 * | 10/2014 | Grotz | A61L 27/54 | 623/20.17 |
| 2014/0350691 A1 * | 11/2014 | Linares | A61F 2/3609 | 623/22.45 |

(56) References Cited

U.S. PATENT DOCUMENTS

| | | | |
|---|---|---|---|
| 2014/0364955 A1* | 12/2014 | Smith | A61F 2/3859 |
| | | | 623/20.28 |
| 2015/0127114 A1* | 5/2015 | Zhao | A61F 2/58 |
| | | | 623/22.13 |
| 2015/0342740 A1* | 12/2015 | Boedo | A61F 2/32 |
| | | | 623/22.15 |
| 2016/0000575 A1* | 1/2016 | Sawyer | A61F 2/442 |
| | | | 623/17.16 |
| 2016/0058559 A1* | 3/2016 | Forsell | A61F 2/32 |
| | | | 623/22.15 |
| 2017/0231777 A1* | 8/2017 | Arramon | A61F 2/4425 |
| | | | 623/17.15 |
| 2017/0266010 A1* | 9/2017 | Bonutti | A61F 2/0077 |
| 2017/0266012 A1* | 9/2017 | Grotz | A61F 2/3859 |
| 2017/0312088 A1* | 11/2017 | Grotz | A61L 27/54 |

* cited by examiner

RESPONSIVE BIOMECHANICAL IMPLANTS AND DEVICES

RELATED APPLICATIONS

This application claims priority to U.S. Application No. 62/440,653, filed Dec. 30, 2016 the disclosure of which is incorporated by reference in its entirety herein.

BACKGROUND

The present disclosure relates generally to bone joint prostheses. More specifically, it concerns embodiments of prostheses for joints or other injured parts of the body which may deliver increased joint stability yet allow for normal flexion and extension motion. Exemplary joints may include the knee, hip, wrist, and elbow, although other prostheses are additionally contemplated within the scope of the invention.

Orthopedic prostheses are commonly utilized to replace damaged bone and tissue in the human body. Artificial joint replacement is a widely accepted successful medical procedure for the treatment of arthritic or deformed joints. Hundreds of thousands of joint replacement procedures are performed every year. Prosthetic hip and knee replacement comprise the vast majority of these procedures; however, many other joints may be treated as well including, but not limited to, the shoulder, elbow, wrist, ankle, and temporomandibular joints. For example, a prosthetic knee implant may be used to restore natural knee function by repairing damaged or diseased articular surfaces of a femur, a tibia, or both. Additionally, there are other joints and residual limbs, such as the intervertebral disk joint of the spine, which are not commonly replaced with prosthetic joints, but which might be amenable to such treatment to remedy disease states if sufficiently durable materials in functional designs were available.

The ideal total artificial joint prosthesis may be characterized in terms of its durability. The mechanical parts of the joint (otherwise known as an articulation) should function without wearing out or breaking. Further, the implant's fixation to the recipient's skeleton should remain rigidly intact for the duration of the recipient's lifetime without requiring restrictions on the intensity of activities or the degree of load bearing beyond those which would apply to a natural joint. Currently available devices fall short of fulfilling these criteria in one or more significant ways.

For example, polyethylene bearings may wear out after between 5 and 20 years of service, depending upon factors such as a patient's age, weight, and activity level. The younger and more active the patient, the shorter the anticipated functional life of the implant. Thus, those patients who, because of their youth, need the greatest durability from their implants, typically receive the exact opposite.

Further, the generation of particulate debris (or wear particles) which results from normal wear often causes inflammatory reactions in the bone surrounding and anchoring the implants, which can result in severe erosion of the bone. The immune system's inflammatory reaction to particulate debris—or "osteolysis"—has proven to be a most prevalent cause of failure of ratification joints requiring subsequent artificial joint replacement. This is because osteolysis may cause loosening of the critical implant-bone fixation, and may result in increased risk of fracture of the bone around the implants. It is also the cumulative effect of continual wear of the polyethylene that results in wear-through of the mechanical joint and ultimate bearing failure.

In order to reduce the risks of dislocation, recipients of artificial joints may be required to restrict their range of motion in normal activities, compromising their ability to engage in many routine activities which would otherwise be possible with normal natural joints. In order to decrease the rate of bearing wear which leads to implant failure and/or problems resulting from debris related osteolysis, patients may also be required to restrict their activities in terms of intensity and duration relative to that routinely possible with normal natural joints.

Unsurprisingly, wear-through of the components and/or periprosthetic osteolysis of the host bone with associated implant loosening and/or periprosthetic bone fracture requires major surgical intervention to remove the failed implants, reconstruct the damaged bone, and replace the failed prosthesis with a new artificial joint. This revision surgery is typically much more complicated than the initial implant surgery, and carries with it increased risks for perioperative complications, as well as increased risks for implant failure as compared to primary artificial joint replacement. Subsequent failures require further complex surgical intervention, with continually increasing risks of perioperative complications and early implant failure with each episode.

Additionally, prosthetics face similar wear-down issues as artificial joints. The ideal prosthetic limb may be characterized in terms of its durability and impact absorption. For example, among the features desirable in a prosthesis is the incorporation of some means for providing impact absorption and/or damping during use of the prosthesis without sacrificing the ability to reliably and predictably support the amputee's body weight. Such impact absorption permits the amputee to participate in activities with comfort and minimal residual limb trauma, hence allowing the amputee to be mobile for longer periods of time. Also desirable is a convenient means to selectively adjust the degree of impact absorption to suit the particular attributes (e.g., weight) and activity (e.g., walking, running, jumping, etc.) of the amputee.

It is an object of the current disclosure to improve upon prior prosthetic technologies for increasing life of an implant and/or a prosthetic by reducing the wear and decreasing the shedding of significant amounts of particles as a result of normal use of the prosthetic and increasing the damping effects of the implant and/or prosthetic.

SUMMARY

The following presents a simplified summary of the invention in order to provide a basic understanding of some aspects of the invention. This summary is not an extensive overview of the invention. It is not intended to identify critical elements of the invention or to delineate the scope of the invention. Its sole purpose is to present some concepts of the invention in a simplified form as a prelude to the more detailed description that is presented elsewhere.

In general, there are two types of artificial joints: articulating joints and flexible hinge joints. Articulating joints include hip, knee, shoulder, ankle and other joints. Flexible hinge joints include silastic and metacarpal-phalangeal joints. Articulating joints typically consist of a hard surface material (e.g., metals such as titanium, aluminum oxide, tungsten carbide, cobalt chrome, nitride silicon carbide, or others materials such as polycrystalline, diamond compact cubic boron, silicon nitride, etc.) mated to a plastic bearing surface (e.g., ultra high molecular weight polyethylene which may be injection molded, hot pressed, highly cross-linked, etc.). Articulating joints may take a myriad of configurations including variations on a ball in socket design, such as with a hip and shoulder joint, and variations on a hinge design such as with a knee, elbow, or metacarpal-phalangeal joint. In every case, the prosthesis is designed to restore, to the greatest extent possible, the functional range of motion and mechanical stability of the affected joint.

Most joint replacements include a convex spherical ball (i.e. femoral head) and a concave socket (i.e. acetabular socket) articulation. Joint replacement consists of replacing the damaged articular surfaces with new articulating bearing surfaces. On one side, a hemisphere-like cup (otherwise known as a socket or bearing surface) is placed in the patient's damaged or worn socket, and fixed by some means to the patient's bone. On the opposite side, the prosthetic replacement consists of a sphere-like ball designed to fit into, and articulate with the prosthetic cup. The sphere-like ball may be a resurfacing device (e.g., designed to fit over the patient's own bone) or may it be mated directly to the bone to provide an entirely new surface. The ball and socket work as a pair in similar fashion to the original joint, restoring a partial range of linear and rotational motion.

For total joint replacement, the most commonly used device consists of a metal head articulation with a high density ultra high molecular weight or cross-linked polyethylene bearing surface. The use of polyethylene avoids metal on metal contact, as there is still concern about wear debris of a metal-on-metal bearing couple. These wear particles from metal-on-metal bearing couples, which may consist of metals such as cobalt-chrome-molybdenum alloy, with large combined surface area may result in significant release of metal ions which may be toxic and has the potential to cause long term carcinogenicity. Long-term clinical studies are required to document the actual risk of this exposure.

It is also known that partial parts of a joint may be replaced. A partial joint replacement is performed when only one of the articulating portions of the joint is damaged, as with avascular necrosis of the femoral head, or in the case of a hip fracture that is not amenable to repair. The damaged portion is replaced with a prosthetic articulation designed to function with the remaining natural biological portion of the joint. The requirements are somewhat different than with a total articular replacement, in that the artificial portion must match the contours of the anatomic segment, and must be conducive to preserving the function of the natural segment. This would include having a surface smooth enough to minimize wear and tear to the natural joint surface, and optimizing surface material properties and contours to encourage entrainment of joint fluid into the joint space.

Implants wear over time due to repeated activity in which components of the implant rub against each other or impact each other with force, thus degrading the material. This impact may be as simple as an implant user engaging in everyday activities such as jumping, walking, running, or a nervous tick that moves their replaced knee joint up and down repeatedly. As described herein, frictional forces (e.g., dampers) may be applied to an object to slow the motion of the resonating frequency and attenuate the amplification or shock of the impact upon the joint as a result of engaging in these activities.

In general, there are two types of prosthetics, before or after the joint, which replace either a partial or complete loss of a limb. A transtibial amputation occurs below the knee; a prosthetic may attach to the intact upper leg. Transfemoral amputation occurs above the knee such that the prosthetic includes lower and upper leg portions including the knee joint. Similarly, transradial amputation occurs below the elbow, and the prosthetic replaces a forearm. Transhumeral amputation occurs above the knee, and the prosthetic replaces the upper and lower arm, including the elbow. In every case, the prosthetic is designed to restore, to the greatest extent possible, the functional range of motion and mechanical stability of the affected limb.

Impact absorption in lower limb prostheses is typically achieved by utilizing two or more elongated telescoping members with a resilient means disposed therebetween (e.g., a spring), a vacuum pump, a hydraulic pump, and/or other such means. Therefore, impact absorption is normally achieved by the utilization of some form of resilient means, such as a spring member or a compressible fluid. Nevertheless, during use, many users of prosthetic devices experience pain, edema, and swelling, especially at to the interface between the prosthetic and the patient's limb.

In one embodiment, a prosthetic includes a socket sized and shaped to situate about a residual limb. The socket has a bearing component located adjacent a distal end of the residual limb. The bearing component has an articulation surface sized and shaped to substantially mate with at least a portion of the residual limb. The articulation surface comprises a damping mechanism having an interaction component, and an elastic component. The elastic component biases the interaction component away from the articulation surface. In use, a force received by the bearing component is partially transferred to the interaction component, thereby causing an alteration in the elastic component, the alteration resulting in at least a partial dissipation of the force.

In another embodiment, a prosthetic joint implant includes a bone implantable component and a bearing component. The bearing component has an articulation surface sized and shaped to substantially mate with at least a portion of the bone implantable component. The articulation surface includes a damping mechanism comprising an interaction component, and an elastic component, wherein the elastic component biases the interaction component away from the articulation surface. In use, a force received by the bearing component is partially transferred to the interaction component, thereby causing an alteration in the elastic component, the alteration resulting in at least a partial dissipation of the force.

Novel and unobvious implantable devices are set forth herein, as will be evident from reviewing the description below and the accompanying drawings.

BRIEF DESCRIPTION OF THE DRAWINGS

The drawings constitute a part of this specification and may include exemplary embodiments of the present invention and illustrate various objects and features thereof.

The invention may be further understood by reference to the accompanying drawings in which.

DETAILED DESCRIPTION

Figure 1:
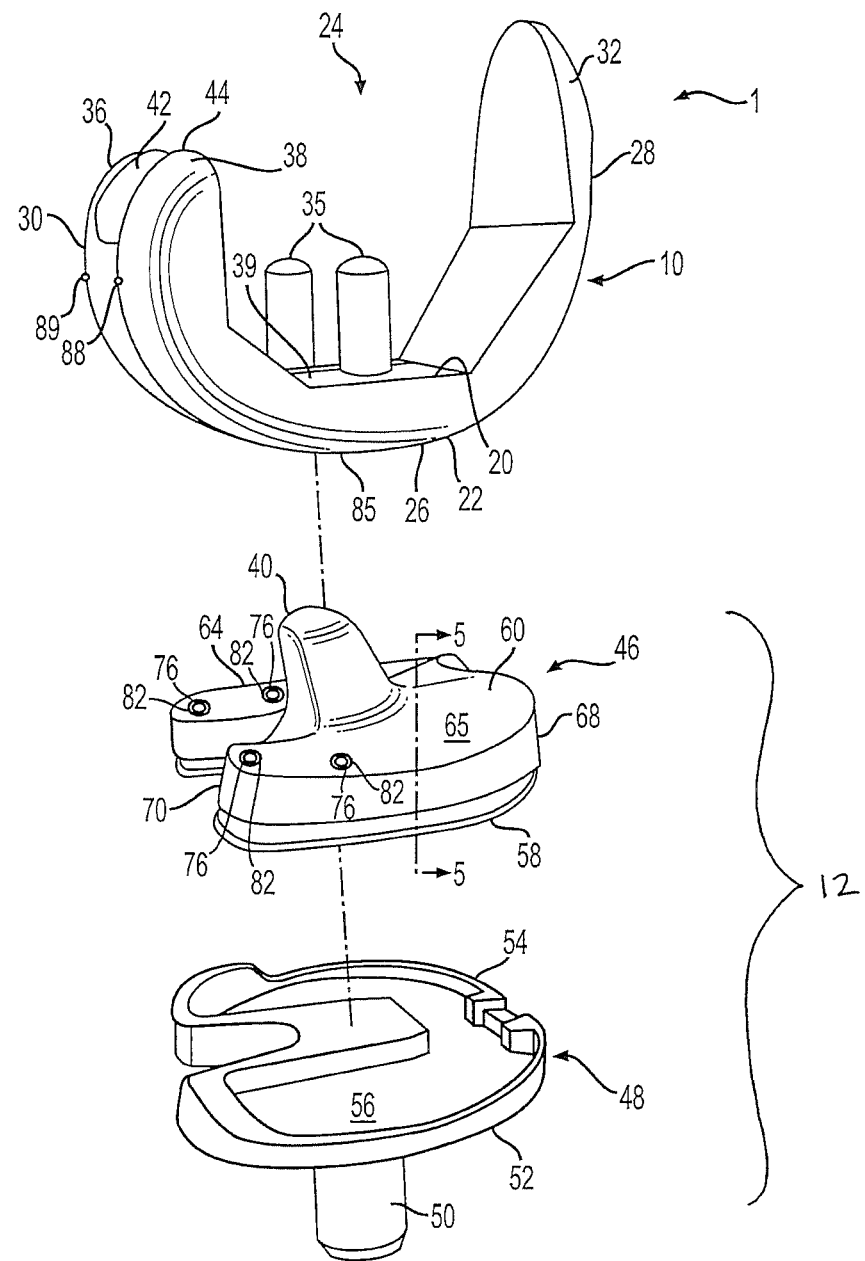
FIG. 1 is a perspective view of a biomechanical implant according to an embodiment of this disclosure.
Figure 2:
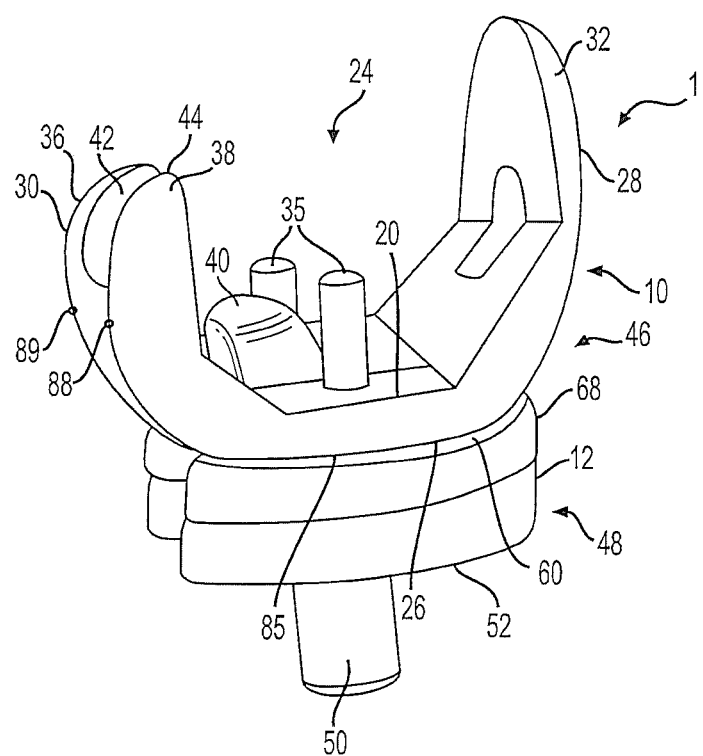
FIG. 2 is an exploded view of the biomechanical implant of FIG. 1.

Reference is now made in detail to exemplary embodiments which are illustrated in the accompanying drawings. It is to be understood that other embodiments may be utilized and structural and functional changes may be made. Moreover, features of the various embodiments may be combined or altered. As such, the following description is presented by way of illustration only and should not limit in any way the various alternatives and modifications that may be made to the illustrated embodiments. In this disclosure, numerous specific details provide a thorough understanding of the subject disclosure. It should be understood that some aspects of this disclosure may be practiced with other embodiments not necessarily including all aspects described herein, etc.

FIGS. 1-5 illustrate a biomechanical implant or device 1 adapted to replace a joint in a human being. In the illustrated embodiment, the joint to be replaced is a knee joint (FIGS. 7A-7B), but it is for exemplary purposes only and not meant to be limiting, as any bone, joint, or other type of implant may be envisioned within the scope of this disclosure. Knee implant devices 1 may include a femoral component 10 which may be implanted on the distal end 9 of a femur 11 (FIGS. 7A and 7B), which articulates with a natural tibia 13 or with a tibial component 12 implanted on the corresponding proximal end 14 of tibia 13. The femoral and tibial components 10 and 12, respectively, may cooperate or be used alone to restore the function of healthy natural knee.

The femur component 10 of a prosthetic knee implant 1, in accordance with at least one example of the present disclosure may be used alone (not shown) or in conjunction with the tibial component 12 to provide a prosthetic knee implant. The femur component 10 may be made in a variety of shapes and sizes to accommodate a variety of patient knee joints and are usually made from metals such as titanium, aluminum oxide, tungsten carbide, cobalt chrome, nitride silicon carbide, etc., or non-metals such as polycrystalline, diamond compact cubic boron, silicon nitride, etc.

Figure 7A:
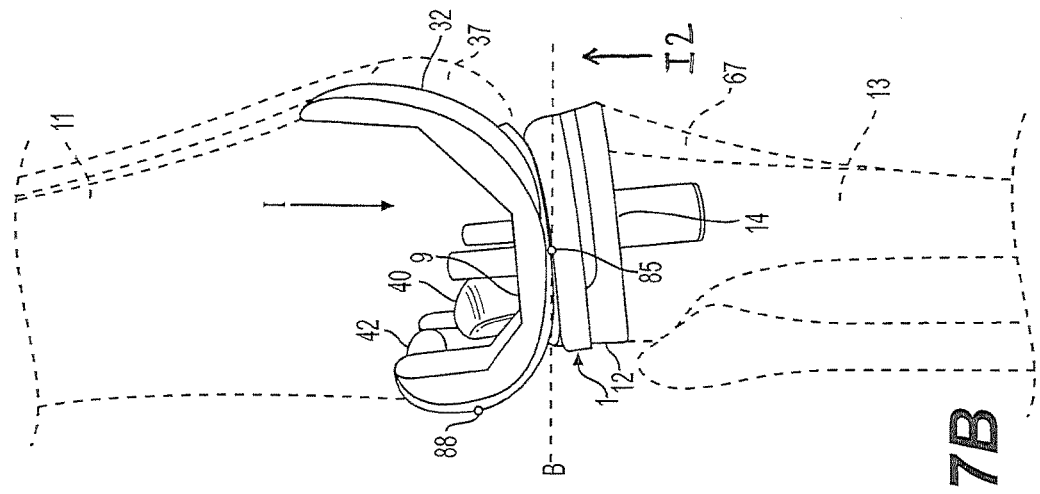
FIG. 7A is a side view of the biomechanical implant of FIG. 1 shown in use with a Femur and a Tibia with the bones shown in phantom and being in a bent configuration.
Figure 7B:
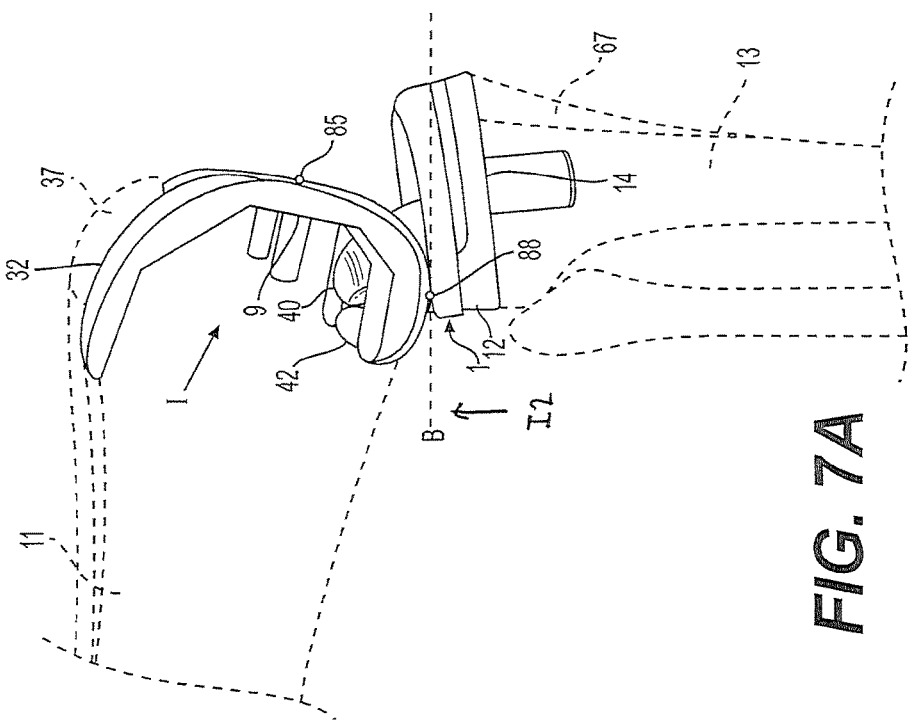
FIG. 7B is a side view of the biomechanical implant of FIG. 1 shown in use with the Femur and the Tibia with the bones shown in phantom and being in a straight configuration.

The femoral component 10 may include a femur-contacting surface 20 formed along an inner periphery of the femoral component 10. The femur-contacting surface 20 may be configured to contact a distal end 9 of the femur 11 (FIGS. 7A-7B). An opposing articulation surface 22 may be disposed opposite of the femur-contacting surface 20. The femoral component 20 may include a proximal portion 24, a distal portion 26, an anterior portion 28, and a posterior portion 30.

The proximal portion 24 of the femoral component 10 may include one or more of fixation pegs 35. The one or more fixation pegs 35 extend from the femur-contacting surface 20. The fixation pegs 35 may be configured to be located within the distal end 9 of the femur 11. In the illustrated example, the femoral component 10 includes two fixation pegs 35.

The anterior portion 28 of the femoral component 10 may include an anterior flange 32. The anterior flange 32 of the femoral component 10 may include a trochlear groove 34 that may define a pathway for a patella 37 (FIGS. 7A-7B). The distal and anterior portions 26 and 28, respectively, may be configured for articulation with a natural tibia 13 or with a prosthetic tibial component 12.

The posterior portion 30 includes two lateral condyles 36 and 38 defining an intercondylar notch 39 between the lateral condyles 36 and 38. As described herein, having the intercondylar notch 39 located centrally between the lateral condyles 36 and 38 may enable a tibial post 40 to pass there through. A posterior cam portion 42 located at the posterior end 44 of the condyles 36 and 38 may act as a stop for the tibial post 40.

Moving on, the tibial component 12 of a prosthetic knee implant 1, in accordance with examples of the present disclosure, may be used alone (not shown) or in conjunction with the femoral component 10 as noted above. The tibial component 12 may include a bearing component 46 and a plate component 48.

Figure 3:
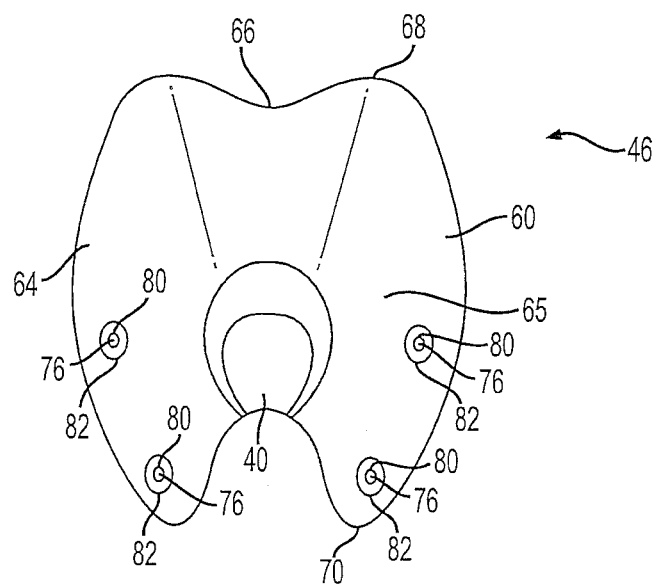
FIG. 3 is a top view of the bearing portion of the biomechanical implant of FIG. 1.
Figure 4:
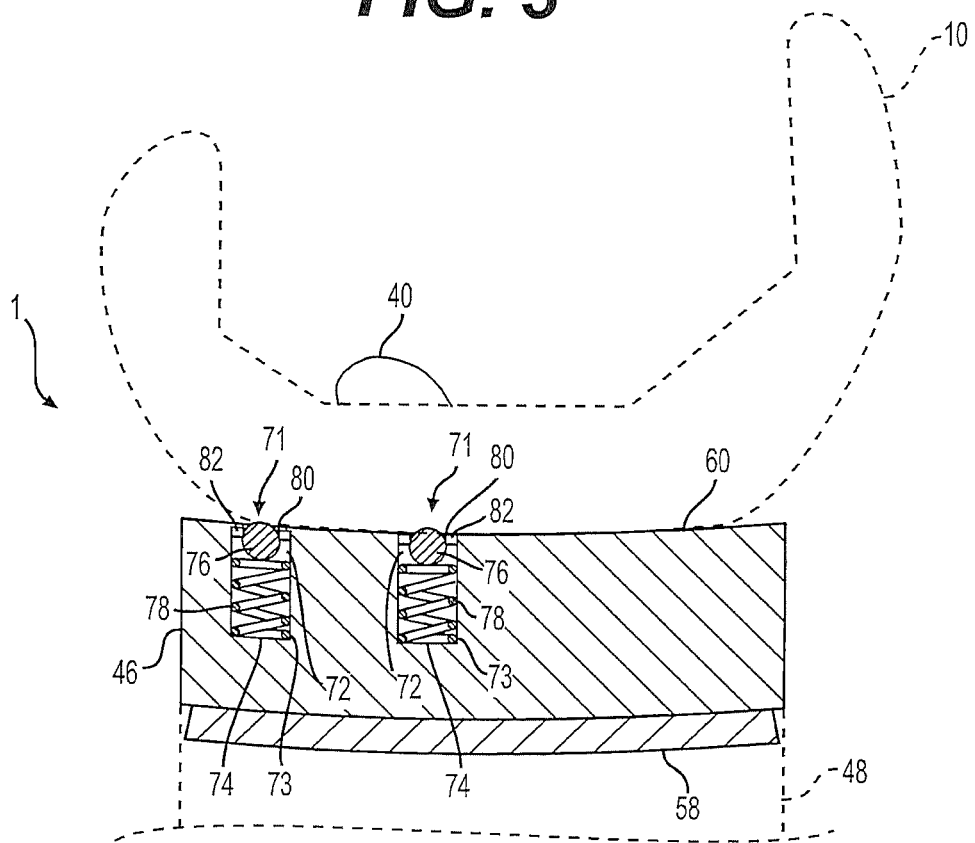
FIG. 4 is a cross section of the bearing portion of the biomechanical implant of FIG. 1 taken along line 5-5 with portions cut away.

Referring to FIGS. 3-4, the bearing component 46 may include an articulation surface 60 having anterior and distal surfaces 64 and 65, respectively, that may be sized and shaped to interact with natural condyles of a femur 11 or prosthetic condyles 36 and 38 of the femoral component 10. An opposing inferior surface 58 may be configured to interact with a superior surface 54 of the plate component 48, described in greater detail below.

A central tibial eminence, protrudence or post 40 may be located between the lateral surfaces 64 and 65. The tibial post 40 extends proximally from the articulation surface 60 of the bearing component 46. The tibial post 40 may be located approximately halfway between the lateral surfaces 64 and 65, or it may be offset by some distance dependent upon the condyles of the femur 11. The tibial post 40 may also be located approximately halfway between a posterior side 68 and an anterior side 70 of the bearing component 46 or offset by some distance dependent upon the intercondylar notch 39 of the femur component 10.

A posterior cutout 66 may be defined in the plate component 48 for the cruciate ligament 67 of the knee joint 1, and may be located at the posterior side 68 between the lateral surfaces 64 and 65, either approximately in the middle or some offset some distance depending on the cruciate ligament 67 of the individual.

It shall be understood by those of skill in the art that the bearing component 46 may be made available in a variety of shapes and sizes in order to accommodate a variety of patient knee joints and may be made from polyethylene processed in many different ways to exhibit various attributes, such as a ultra-high molecular weight or a high degree of crosslinking. The joints may further be injection molded, hot pressed, etc.

As illustrated by the figures, the bearing component 46 may be located atop of, and configured to interact with, the plate component 48. The plate component 48 may include a tibial-contacting surface 52 to contact the tibia (resected) 13 and an opposing superior surface 54, which interacts with the bearing component 46. The plate component 48 may further include a recessed portion 56 that mates with bottom surface 58 of the bearing component 46.

More specifically, the superior surface 54 of the plate component 48 may contact the inferior surface 62 of the bearing component 46. The bearing component 46 and the plate component 48 may be coupled to or engaged with each other via any of a variety of methods. In one example, either the superior surface 54 of the plate component 48 or the inferior surface 58 of the bearing component 46 may include one or more projections 68 that may be received by a corresponding cavity or recess 56 in the corresponding superior surface 54 of the plate component 48 or the inferior surface 62 of the bearing component 46. It is foreseen that adhesives may be added within the recess 56, such as non-reactive, reactive, bio-adhesives, or synthetic adhesives to further secure the bearing component 46 and the plate component 48.

The plate component 48 may additionally include a stem component 50, which may be attached or integral to the plate component 48, and may be used to secure the plate component 48 to the tibia 13 (FIGS. 7A-7B). The stem component 50, like the fixation pegs 35, must be securely anchored to the recipient's bone to function properly. This fixation may be achieved through the use of cementing agents, typically consisting of polymethylmethacrylate cement, through biological fixation techniques including direct osseointegration to metal or ceramic fixation surfaces and bone ingrowth into porous surfaces on implant surfaces, or through a mechanical interference press fit between the implant and the host bone.

It shall be understood by those of skill in the art that the plate component 48 may be made in a variety of shapes and sizes in order to accommodate a variety of patient knee joints and may be made from metals such as titanium, aluminum oxide, tungsten carbide, cobalt chrome, nitride silicon carbide, etc., or non-metals such as polycrystalline, diamond compact cubic boron, silicon nitride, etc.

Referring to FIGS. 7A-7B, in use, the device 1 may be adhered to a tibia 13 and to a femur 11 as described above. The device 1 is shown in a straight leg configuration in FIG. 7B and a bent leg configuration in FIG. 7A. When the femoral component 10 is flexed or rotated approximately 90 degrees about the plane B (as illustrated in FIG. 7B), posterior-most points 88 and 89 may be positioned at locations to contact the bearing component 46. Upon transitioning from one position to the other, the bearing component 46 receives an impact force I at least along a plane B that is tangential to distal-most points 85 of the lateral condyles 36 and 38 (FIG. 7A-7B). It shall be noted that it is not assumed that the distal-most points 85 are equal, as each individual has a unique anatomy.

A set including different sized femoral components 10, tibial components 12, or both, may be provided, such as in a kit, to allow for varying levels of customization.

Referring now to FIG. 4, a damping mechanism 71 may be located along at least one of the lateral surfaces 64 and 65 of the bearing component 46. In one embodiment, the damping device 71 may include an interaction component 76 and an elastic component 78. The damping device 71 may be positioned in a cavity 72 defining an inner surface 73 and a bottom surface 74. The cavity 72 may be situated anywhere on the articulation surface 60, and in one embodiment, may be positioned on the articulation surface 60 in the approximate area where a distal most point 85 of the condyles 36 and 38 is located. The interaction component 76 may be disposed at least primarily inside the cavity 72, and the elastic component 78 may be similarly disposed in the cavity 72, and may be configured to urge the interaction component 76 toward an upper aperture 80 in the cavity 72. The elastic component 78 may be a helical spring. Other types of resilient elastic components may alternately (or additionally) be used in different embodiments, such as a flat spring, a gas spring, a hydraulic spring, or a magnetic spring. The elastic component 78 may be made from any appropriate material. Further, the elastic component could be a foam material, or any other type of substance that exhibits elastic properties sufficient to provide damping capabilities as described herein.

In the illustrated embodiment of FIG. 4, the upper aperture 80 is round and smaller than the interaction component 76, such that the interaction component 76 cannot completely pass through the upper aperture 80. This may be accomplished by an endcap 82 or other means that is added to the cavity 72 to make the upper aperture 80 smaller and prevent the interaction component 76 from exiting the cavity 72.

The cavity 72 may include threading, and the endcap 82 may include complementary threading for coupling the endcap 82 to the cavity 72, or to the bearing component 46. The endcap 82 may further include a passage or other element for receiving a driver bit to allow the endcap 82 to be fastened to the cavity 72 or to the bearing component 46. Alternately, the endcap 82 may be snapped on, fused, adhered, friction fit, or otherwise attached to either the respective lateral surface 64 or 651 or to the cavity 72 itself.

In one embodiment, it may be desirable for the endcap 82 to be adjustably coupled (e.g., such that it can move up and down). Such adjustment may allow an amount of force on the interaction component 76 provided by the elastic component 78 to be altered as desired. It may additionally (or alternately) be desirable for the stiffness of the elastic component 78 to be adjustable (e.g., via an adjustment mechanism, such as a screw) such that the elastic component 78 may dissipate varying degrees of impact forces, as described below.

It may be desirable for the interaction component 76 to be generally spherical to provide a single point of contact between the interaction component 76 and the femur component 10, or the femur 11 itself with which the device 1 will be used. Nevertheless, it is foreseen that the interaction component 76 may be configured to be shaped differently and the upper aperture 80 may be shaped complementary to the configuration of the interaction component 76.

The interaction component 76 may be constructed of entirely non-elastic material (e.g., metal). However, it may be desirable for the interaction component 76 to be made at least partially of a resilient material such as rubber, or other materials such as polyethylene. In one embodiment, the interaction component 76 may be composed of the same material as the bearing component 46.

In use, the elastic component 78 biases the interaction component 76 toward the aperture 80, and the interaction component 76 extends partially through the aperture 80 and contacts the articulation surface 22 of the femur component 10 or the femur 11 (or the condyles 36 and 38, when the joint is in a bent configuration). When an impact force I is received by the joint 1, for example, as a result of movement of the joint 1, force I may cause the interaction member 76 to press against the elastic component 78 in the direction of the force I, which may further cause the elastic component 28 to compress. It shall be noted that the elastic component 78 may be compressed a small degree or a large degree, depending on the force I. For example, during every day walking activity, the degree of compression of the elastic component 78 may be minimal as compared to the degree of compression of the elastic component 78 when the recipient is running on hard pavement.

When the elastic component 78 compresses, a portion of the force I is absorbed by the elastic component 78. As the elastic component 78 returns to its initial position (e.g., as a result of its elastic properties), the elastic component 78 causes an opposing force, I2, on the interaction member 76 which is subsequently transferred back to the articulation surface 22 of the femur component 10, or the femur itself 11 (as the case may be). However, the amount of force I2 transferred back to the femur component 10 (or the femur 11), is less than the force I that was initially received. This may be due to inefficiencies in the elastic component 78, for example, which prevents all of the force I from being transferred back to the femur component 10. In this way, the force I that is received by the joint 1 may be lessened, thus increasing the life of the joint.

It may be particularly advantageous if multiple damping mechanisms 71 are used with the device 1. In the illustrated embodiment of FIGS. 3-4, there are four damping mechanisms 71. If multiple damping mechanisms 71 are used, the timing of the force transfer may vary slightly, allowing forces I2 to be transferred back to the femur component 10 at different times. Over time, the femur component 10 may be able to withstand this staggered return of forces better than a "constant" return of force from a single damping mechanism 71.

To further dissipate the impact force I and diminish movement of the interaction component 76, a cushion may be placed in the cavity 72 (e.g., on an underside of the endcap 82). In such embodiments, the cushion may be made from a material such that it is initially compressed when the interaction component 76 is in its initial position, contacting the femur component 10. Upon movement of the interaction component 76 away from the aperture 80 (and the cushion) as a result of a force I, the cushion will expand. The cushion may then absorb some force from the interaction component 76 when the interaction component 76 is returned to the femur component 10, causing the cushion to return to the compressed configuration. The cushion may be constructed of, for example, open celled polyurethane, and fast-recovery memory foam may be particularly useful. Those skilled in the art will appreciate that other materials which may quickly return to their original configuration after being compressed may similarly be used.

The damping mechanism 71 may alternately or additionally be incorporated into other areas of the device 1. For example, the damping mechanism 71 may be located in the stem component 50 and/or the fixation pegs 35 to dampen forces on the bone to which the component 50 and/or the pegs 35 are attached. The damping mechanism 71 may be incorporated into other parts of the device 1 as well.

Figure 5:
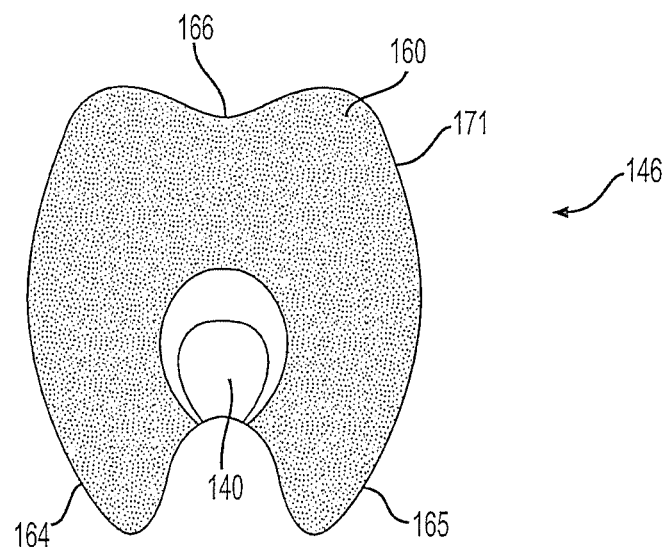
FIG. 5 is a top view of the bearing portion of the biomechanical implant in a second embodiment.
Figure 6:
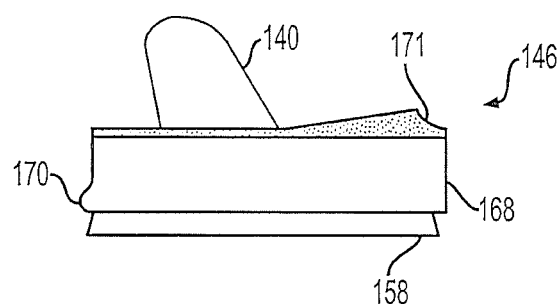
FIG. 6 is a side view of the bearing portion of the biomechanical implant in the second embodiment.

In addition to, or as an alternative to, the damping mechanism 71, the device 1 may have one or more areas having a damping composition applied or adhered thereto. Embodiments of damping compositions are further set forth in U.S. patent application Ser. No. 15/365,923, which is incorporated herein by reference in its entirety. With reference now to FIGS. 5-6, in one embodiment, a bearing component 146 is shown that is substantially similar to bearing component 46, except as illustrated and described herein. In the illustrated embodiment of FIGS. 5-6, a damping composition 171 is provided atop the articulation surface 160. The composition may be any of a number of different compositions, including but not limited to adhesives, paints, coatings, etc. While the embodiment discussed herein refers to the composition 171 as applied to the articulation surface 160, it shall be understood that the composition may be applied nearly anywhere on the joint 1 to disperse and diffuse forces received by the joint 1.

In one embodiment, the damping composition may be a composition having a plurality of 3D nanostructures dispersed throughout. The 3D nanostructures may be mixed into a composition (or into layers of a composition) to create a suspension, wherein the 3D nanostructure is suspended in the composition. Alternately, as described below, the 3D nanostructure may be provided as part of a backing, wherein a conventional adhesive is applied to one side of the backing, the backing having 3D nanostructures dispersed therein, and therefore through the backing, provides a damping effect.

Figure 9:
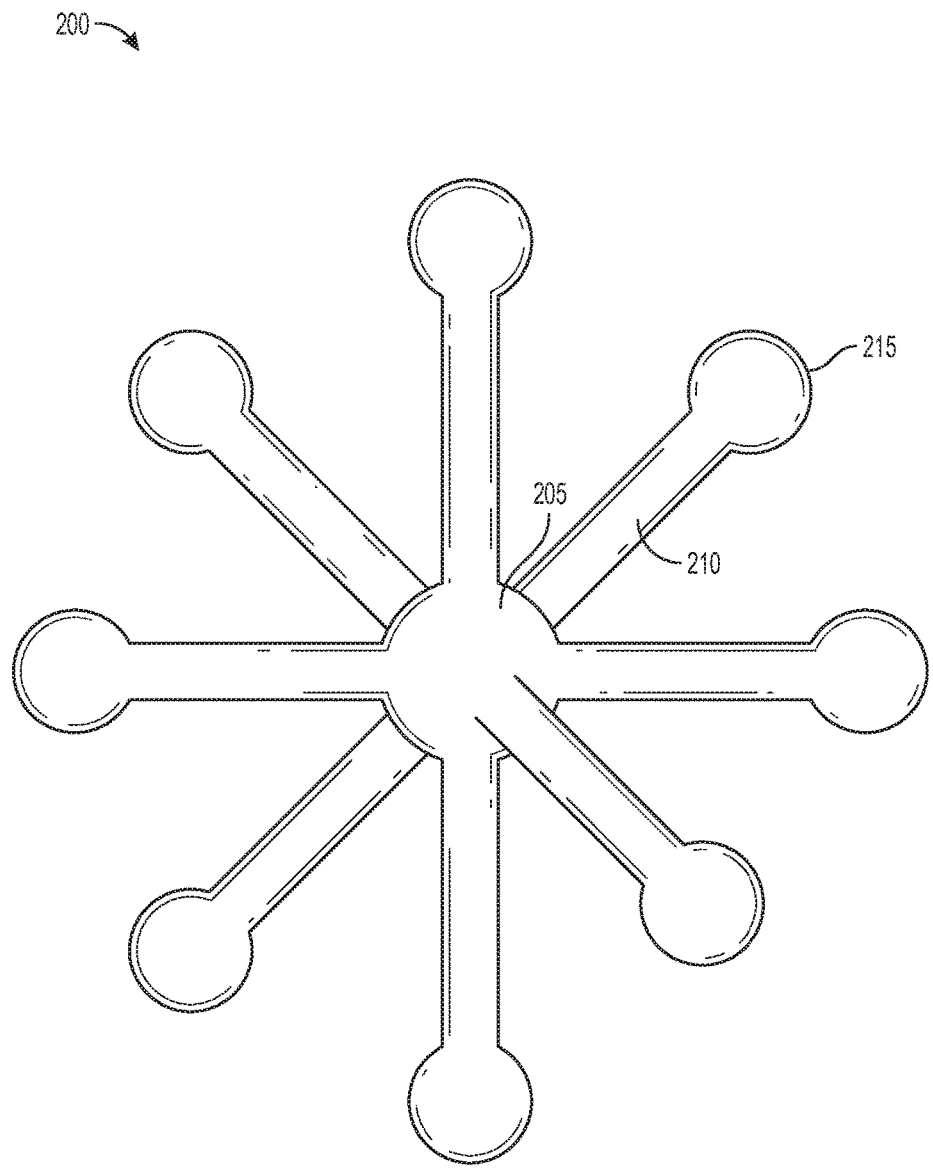
FIG. 9 is a perspective view of a particle for incorporation into a composition for use with a biomechanical device.

FIG. 9 illustrates a 3D structure 200 according to one embodiment. The three-dimensional structure 200 may include a core 205 and a plurality of spokes 210 extending radially outwardly from the core 205. The spokes 210 may extend outwardly at a variety of angles. The structure 200 may be formed of one or more materials which give the nanostructure 200 damping characteristics. Referring to the structure in FIG. 9, the spokes 210 may optionally include interface elements 215 which may come into contact with one or more substrates as described below, or may simply be in contact with the adhesive 105. The interface elements 215 may be useful for expanding the surface area of the contact point between the nanostructure 200 and the substrate to ensure maximum damping effect.

The spokes 210 (and optionally the core 205 and/or interface elements 215) may be formed from a material exhibiting superior flexibility and elasticity, such as thermoplastic polyurethanes (e.g., TPU 92A-1). Thermoplastic urethanes may exhibit durable elasticity, high resistance to dynamic loading, high abrasive resistance, quick response, and good temperature range. In one embodiment, the core 205, and optionally the interaction elements 215, may be formed of a material that exhibits greater stiffness than the spokes 210. In another embodiment, the core 205, and optionally the interaction elements 215, may be formed of a material that exhibits less stiffness than the spokes 210. In still another embodiment, the entire 3D structure 200 is formed of the same material. It shall be understood that any 3D molecule exhibiting acceptable flexible and elastic properties may serve as the structure.

In use, a plurality of 3D structures 200 may be combined with a desirable composition to form a suspension. The 3D structures 200 may be dispersed evenly throughout the suspension for maximum effect. The 3D structures 200 may thus be applied to the substrate with the composition.

Due to the elastic nature of some of the materials that may be used to form the structures 200, the structures 200 may have a tendency to remain in a naturally expanded state. When a change in the environment of the composition 171 occurs, e.g., due to the force I on the device 1, the force I causes the structures 200 to temporarily flex or compress. As a result of the compression of the structures 200, some of the force I is diffused from the bearing component 146 and transferred to the structures 200. The structures 200 may eventually return to their natural expanded state, and in doing so, return an opposing force I2 to the femur component 10. The opposing force I2 returned to the femur component 10 may be less than the original force I. Due to the structures' 200 ability to diffuse some of the force I from the bearing component 146, the wear on the bearing component 146, the likewise the femur component 10, may be lessened. Similar to the interaction component 76, the amount of compression experienced by the structures 200 may be directly related to the strength of the force I.

In an alternative embodiment of a 3D particle, the particle takes the form of a spheroidal molecule, geodesic dome, or other 3 dimensional shape. Many such particles exist in nature, or have previously been developed, for various applications. Fullerenes are one example of a 3D nanoparticle for use in the invention. Fullerenes are a class of allotropes of carbon which are essentially sheets of graphene which can be rolled into tubes or sphere. One example of a fullerene molecule, C60, comprises 60 carbon atoms arranged as 20 hexagons and 12 pentagons to form a soccer ball (or buckyball) shaped structure. Graphene, for example, may be also be provided as a box-shaped nanostructure (e.g., as a layered structure). A nanotube—where the graphene molecules have been rolled into a 3 dimensional tube, is another example of a 3D nanoparticle. A suspension of nanotubes in a composition may result in the nanotubes being dispersed in various orientations, e.g., some oriented vertically, some oriented horizontally, and some oriented at various angles. In this way, the nanotubes may be effective to dampen forces I received from any angle.

A dendrimer is another example of a 3D nanoparticle. Dendrimers are spherical polymeric materials whose properties are usually determined by functional groups appearing on the molecular surface. Dendrimers may be used in the synthesis of monodisperse (i.e., uniform) metallic nanoparticles. Poly(amidoamine) dendrimers are often used, and the end result may be a dendrimer-encapsulated nanoparticle.

The spheroidal, geodesic dome or other 3D structures (whether they be nanoparticles, microparticles, or other 3D structure) may function substantially similarly to the 3D structure 200 discussed above. For example, in the case of C60, the bonds between carbon atoms may have some degree of flexibility which allows the molecule to flex or compress when energy is applied to the molecule. It shall be understood that the spheroidal, geodesic, and other 3D structures described herein are exemplary only, and that other 3D structures having similar or compatible properties may additionally be utilized and are contemplated within the scope of the invention.

In one embodiment, it may be preferable for the nanoparticle 200 to exhibit magnetic properties. When suspended in an adhesive, the adhesive may take the form of a ferrofluid, or a liquid (liquid, gel, plasma etc.) that becomes magnetized in the presence of a magnetic field. As will be described in greater detail below, ferrofluidic adhesives may allow for passive and/or dynamic response to a force I.

Ferrofluid is a unique material that acts like a magnetic solid and like a liquid. Here, by incorporating 3D damping apparatus having magnetic properties into an adhesive, the adhesive may be transformed into a ferrofluid. A ferrofluid is superparamagnetic, which is a property that may only exist at the nanoscale level, allowing the liquid to display magnetic tendencies only in the presence of a magnet. Thus, in order to transform an adhesive from a liquid to a ferrofluid, the composition 171 must have magnetic properties.

Carbon-based 3D structures, such as C60, may be naturally paramagnetic, i.e., behaves like magnets in the presence of a magnetic field. Other 3D structures, such as those manufactured from a polymer, may be coated in, or otherwise incorporate a magnetic material such as iron oxide. It may be desirable for the magnetic material to be coated in a surfactant to keep the magnetic structures from sticking together.

Absent a magnet, the 3D structures may function as described above. In other words, without a magnet, the 3D structures may simply compress as a result of an applied energy, thus diffusing some of the applied energy away from the substrate. In the presence of a magnetic (or electric) field, however, the adhesive may become an even more effective damper.

A ferrofluid is superparamagnetic, which is a property that may only exist at the nanoscale level, allowing the liquid to display magnetic tendencies only in the presence of a magnet. Ferrofluidic adhesives may allow for passive and/or dynamic response to applied energy to a substrate.

Without a magnetic (or electric) field, the 3D structures in the composition 171 may simply compress as a result of a force I, thus diffusing some of the force I away from the bearing component 146. In the presence of a magnetic (or electric) field, however, the composition 171 may become an even more effective damper.

Figure 8:
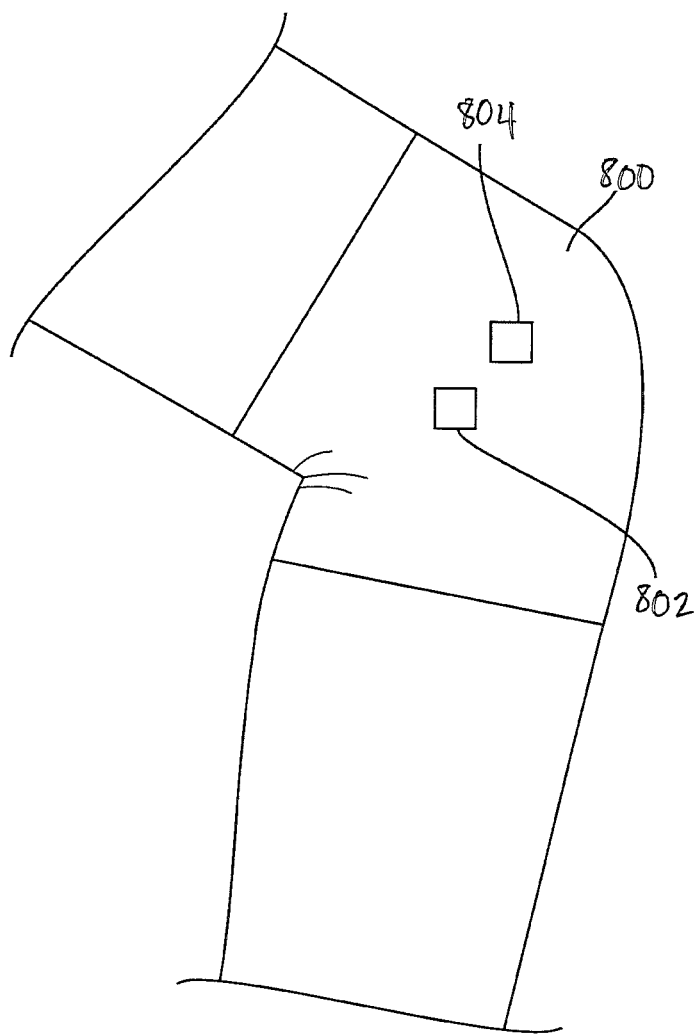
FIG. 8 is a side view of a leg with a knee wrap having a transmitting circuitry.

Referring now to FIG. 8, a magnetic field (e.g., using a magnetized or magnetizable wrap 800), may be applied evenly at or near the areas of the joint 1 having the composition 171 to influence the orientation and/or stiffness of the 3D structures. This may be most useful in the case of a composition suspension comprising nanotubes. The wrap 800 may further include sensors 802 (e.g., accelerometers, ohmmeter, motion, hall effect, thermocouples, p-n junctions, Peltier junctions, etc.) which may aid in determining where the magnetic field should be applied. For example, the sensors 802 may be able to determine the degree of flexion of the joint 1, and may be configured to provide a signal to activate an area of the wrap 800 in order to magnetize it. The 3D nanoparticles in the composition 171 may react accordingly.

The magnetic fields described above may generally be considered static or passive because the magnetic field, when applied, is steady state. In other words, the magnetic field may be turned on, or off, but the magnetic field may not vary, for example, over time, or in response to dynamic changes in the joint environment, as will be further discussed below.

However, in still another embodiment, the composition 171 may be configured for dynamic response to changes in the joint environment in real time. Here, multiple sensors 802 may be provided. As the sensor(s) determines, for example, movement, the sensor(s) may communicate with a processor 804, which may be equipped with a program stored on memory (not shown) with instructions for evaluating the data received from the sensors and to transmit a signal (e.g., using a wireless connection over a network, Bluetooth, wired connection, or any other method whether now known or later developed) to the wrap 800 such that the wrap 800 may magnetize in various concentrated sections to alter the properties of the composition 171 (e.g., change in orientation, elasticity, etc. of the 3D structures). For example, one sensor may communicate to the wrap 800 in a first concentration section that the magnetic field should have a certain strength. Another sensor may communicate to the wrap 800 in a second concentration section that the magnetic field should have another certain strength. Together, these sensors 802 may allow for the joint 1 to operate most effectively based on the orientation of the joint by defining the strength of the 3D nanoparticles in each area.

The magnetic field may alter the properties of the composition 171 (e.g., change in orientation, elasticity, etc. of the 3D structures) in such a way that the 3D structures in the composition 171 experience a degree of physical displacement at controlled timing intervals based on the frequency spectrum of the force (i.e. jumping, running, walking, etc.). In one embodiment, the 3D nano structures in the composition 171 may actually experience controlled oscillations (e.g., physical displacement along a particular distance). The controlled response of the nano structures in the composition 171 may result in a response force I2 that is in a spread spectrum inverse waveform which may geometrically stabilize the joint 1 to avoid peak resonant frequencies which may damage the femur component 10, and the bearing component 46. In other words, the controlled adjustments and corresponding response of the 3D structures in the composition 171 may result in a decrease of the amplitude of the force I by spreading the applied energy out over time and thereby increasing the life of the implant 1.

It shall be noted that other forms of wraps are envisioned within the scope of this disclosure, such as watches, wrist wraps, elbow wraps, even cellular phones through application management.

In still another embodiment, the 3D structures 200 may be electrically active damping apparatus, and the composition may act as an electrically insulating fluid so as to form an electrorheological composition. Applying an electric field (low voltage) at or near the substrate to influence the 3D structures (e.g., via the wrap 800) may allow for a change in the apparent viscosity or the durometer of the composition 171. An electric field may be applied at or near the composition 171 using known techniques. The apparent change in the viscosity of the composition 171 may be directly dependent on the strength of the applied electric field. Thus, as the strength of the applied electric field is increased and/or decreased, the consistency of the composition 171 may transition from that of a liquid to a gel, and vice versa (or to and from a more elastic gel to a less elastic gel).

The change in viscosity or durometer of the composition 171 may occur over very small time increments, e.g., milliseconds, making the electrorheological composition especially useful in conjunction with sensors (e.g., sensors 802). The sensors may measure force (e.g., movement, acceleration, etc.) of the joint 1. If the sensor senses a force over a threshold value, the sensor may transmit a signal to cause an electric field to be applied to the wrap 200. In response, the composition (via the 3D structures) may become stiffer in order to reduce the effects of the force.

While reference is made herein to magnetic fields and electric fields, it shall be understood that the magnetic fields and electric fields may additionally or alternately be other types of force fields which may be used to alter the properties of the 3D structures. For example, force fields such as subsonic, ultrasonic, electromagnetic, or photonic fields may be applied (using methods known by those skilled in the art) in conjunction with the composition having damping apparatus.

In still yet another embodiment, the 3D structures may take the form of piezo elements. In response to a force I, the piezo element may become deformed. For example, when the piezo element 200 is bent in one direction due to the force I, a force field (as described above) may be activated (e.g., via a signal from a sensor) to send electric power to the piezo element to bend in the other direction. In this way, the response of the piezo element may help to reduce wear of the joint 1. The piezo element may also be useful for acquiring position readings as an input sensor device or an array of devices at varying angles.

It shall be understood that hybrid control/sensory modes may provide sensor and control functionality within the same physical element. For example, a piezo element can be configured to both sense and monitor motion and frequency data at one moment in time. Additionally, the same piezo element may be dynamically switched into a controlled response actuator in order to influence and overcome undesirable movements within the joint.

As noted briefly above, the 3D structure may alternately (or even additionally) be provided in a backing. One example includes an adhesive with a backing. A principal portion (e.g., backing) may consisting of foam (or other similar material) and adhesive 105 is applied to one or more sides of the principal portion 305. Any of the 3D damping apparatus described herein (or other appropriate 3D structure) may be incorporated into the backing 305. Further, the 3D structure(s) provided in the backing may be configured for dynamically controlled response as a reaction to a force field, as discussed above.

Variations of arrangements including combinations of hybrid configurations of smart-materials such as nickel titanium or nitinol can be combined to perform dynamic response by utilizing the properties of shape-memory alloys (SMAs). SMAs and other smart-materials may exhibit properties that allow the molecular alignment to change in physical state (i.e. relative molecular position) based on variations in energy levels experienced by the SMA material. For example, in the form of a wire strand, nitinol varies in length based on the temperature of the SMA itself. In the case of conductive smart-materials such as nitinol, an electric current can be induced into the smart-material/SMA in order to alter the temperature of the SMA—causing the length of the wire to vary based on changes in the wattage dissipated across the SMA wire within the adhesive structure.

Variations of state, position, and structure within SMAs and smart-materials can be exploited to embed SMA wires, pellets, or thin-film strips within the composition 171. By varying the SMA's density, position, and relative placement between companion nanoparticles the effective resonant mode of the composition 171 can be changed based on external stimulus as a controlled response to achieve damping.

SMA pellets can be dispersed within a mixture of 3D structures 200 to create a layer which may have various properties (e.g., fluid, gel, plasma, etc.) that can be altered in dimension based on externally induced waveforms (e.g., force I). The layers may be provided, for example, on the articulation surface 160 of the bearing component 146. Direct contact of the external response waveforms or force fields can be conductive as direct current (DC) or low-frequency. Indirect induced waveforms can also be used to capacitively couple electrical energy through the SMA pellets using strategically selected high-frequency alternating frequency (AC) waveforms which do not require direct electrical contract. In other words, a nearby field of energy can be utilized to vary the anti-resonant damping mode of the adhesive without any direct contact to the adhesive itself.

Smart-materials can be somewhat slow to respond due to the thermal mass or other physical properties that can slow response time. This means that there is a limit to the response time (or frequency) of the molecular changes in the smart-material (or SMA) itself. One method of obtaining increased performance is to utilize a harmonic frequency byproduct (based on the changes in the physical properties of the SMA material) to assist in the anti-resonant damping process. For example, a change in SMA structure may be possible in 100's of milliseconds occurring in a repetitive pattern at a fundamental frequency (or rate of change) altering the SMA structural alignment. A resonant byproduct of this movement-pattern can be realized by strategically using the 3rd (or 5th, etc.) harmonic with notable energy that can be used to assist in the anti-resonant tuning and detuning of the adhesive structure for damping. By utilizing a higher frequency harmonic as the controlled response damping, you can achieve this result by providing a much lower rate of change to the molecular smart-material/SMA and achieve higher frequency movements in the substrate structure for damping. The net result allows slow movements within the composition 171 to provide damping to higher frequency vibrations which in turn enhance damping performance of the composition 171.

In embodiments where force fields (magnetic, electric, etc.) are employed, care may be taken to ensure that the system does not interfere with the body itself, or with other electrical systems that may be employed within the body (e.g., pacemakers). For example, customizable polymer coatings may provide inert biocompatibility that may be surface-applied within a plasma chamber. Isolation of the body from electrical conductivity and chemical compatibility may thus be achieved. Additional beneficial byproducts of such polymer coatings include the ability to achieve a high-level of anti-rejection by the human body. In another example, band pass filters may be employed in order to avoid unwanted interferences.

Figure 10:
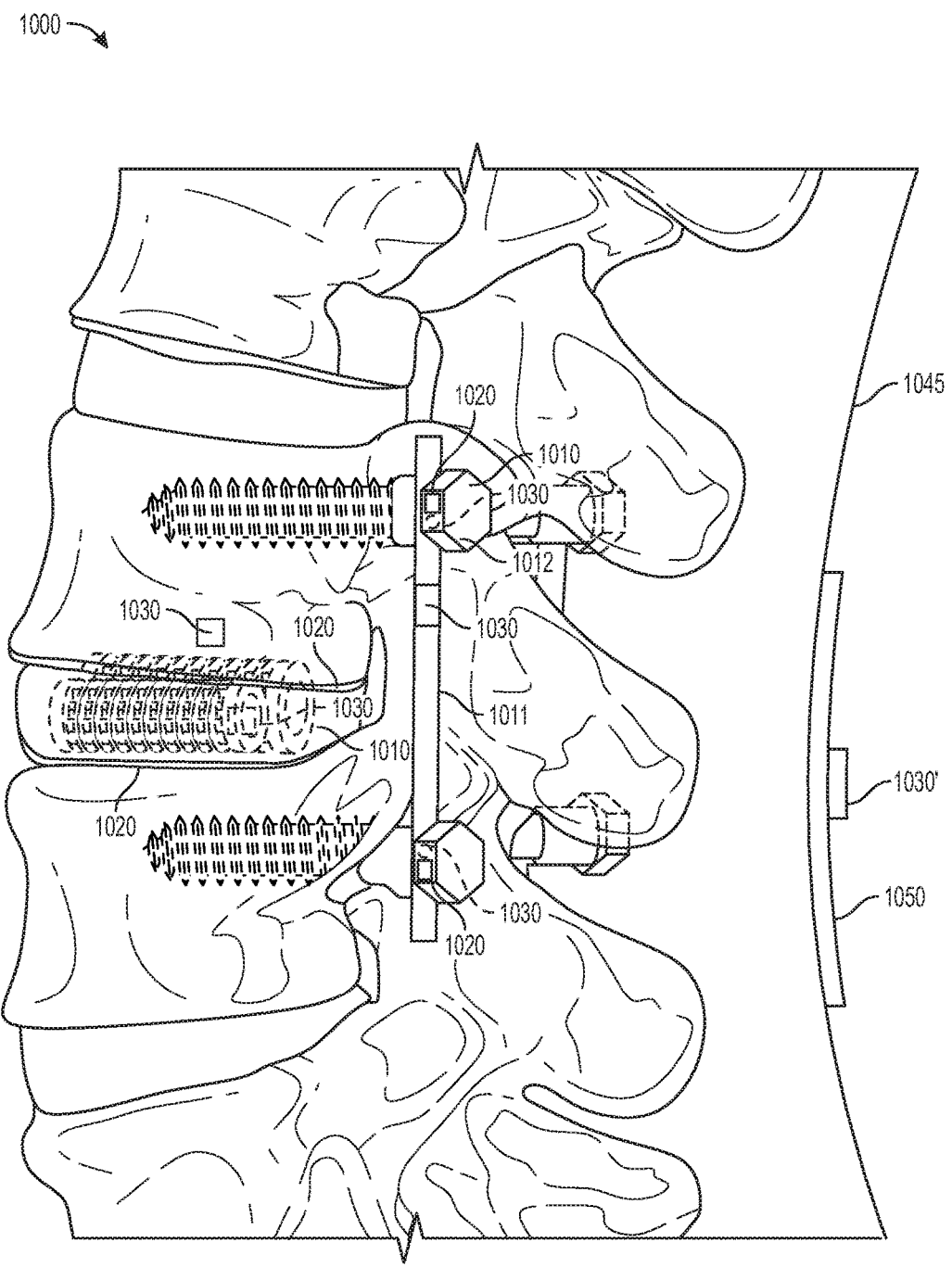
FIG. 10 is a side view of a biomechanical implant shown in use as a portion of a patient's spine according to another embodiment of the invention.

The description above is directed to an exemplary embodiment of the invention as it applies to a knee joint. However, it shall be understood by those of skill in the art that damping apparatus may beneficially be incorporated into other replacement joints and/or prosthetic devices. Referring now to FIG. 10, a portion of a spine 1000 is shown incorporating multiple types of spinal implants 1010 and a rod 1011. The spinal implants 1010 may each have a damping apparatus 1020 incorporated at any desirable location in or on the spinal implant 1010 or rod 1011. This includes the interior surface (not shown) of the horse shoe shaped rod receiver 1012 of the spinal implant 1010. The damping apparatus 1020 may be configured as any of the damping apparatus 1020 described herein (e.g., the damping apparatus 71, or a composition such as a coating, adhesive, etc.) Accordingly, especially in the case of a composition, the apparatus 1020 may be magnetically or electrically effected as described above, and sensors 1030 and 1030' may be incorporated at or near the implants 1010 (e.g., within the body 1030 or on the outside 1030', for example, in a patch 1050 worn by the patient 1045) to effectuate changes in the composition 1020.

The sensors 1030 and/or 1030' may be configured to allow the spinal implants 1010 (and/or other biomechanical devices) to function in an array as a distributed system for better operation of the implants 1010. The sensors 1030 and/or 1030' may communicate with each implant damping apparatus 1030 individually and/or may communicate with the implants (via the damping apparatus 1030) as a system. For example, the sensors 1030 and/or 1030' may sense that a particular activity is occurring that is affecting the person in a particular way. If the sensors 1030 and/or 1030' sense that one implant 1010 is receiving more applied energy than another, than then sensors 1030 and/or 1030' may communicate to the damping apparatus 1020 to take action according to the amount of energy received. Each implant 1010 may thus act separately, but yet together as a system, to ensure that the patient is receiving superior results from the implant 1010.

Those of skill in the art shall further understand that a distributed system may utilize multiple sensors and control points to determine resonance and function as an overall system throughout the human body. In other words, many joints, prosthetics, and/or sensing control points throughout the body may work together as an overall system to achieve superior performance beyond the capabilities of a single joint. For example, the spinal implants 1010 and related sensors 1030 and/or 1030' may be in communication with other sensors and implants (e.g., the device 1) in order to effectuate further achievements of the system. If sensors 802 used in connection with the device 1 (e.g., as a knee implant) sense that the patient is running, the sensors 802 may send a signal to the sensors 1030 used in connection with spinal implants 1010 in order to take preventative measures (e.g., provide a controlled response of the composition 1020 such as softening the composition to allow for greater impacts) to prevent extra wear on the spinal implants 1010.

Figure 11:
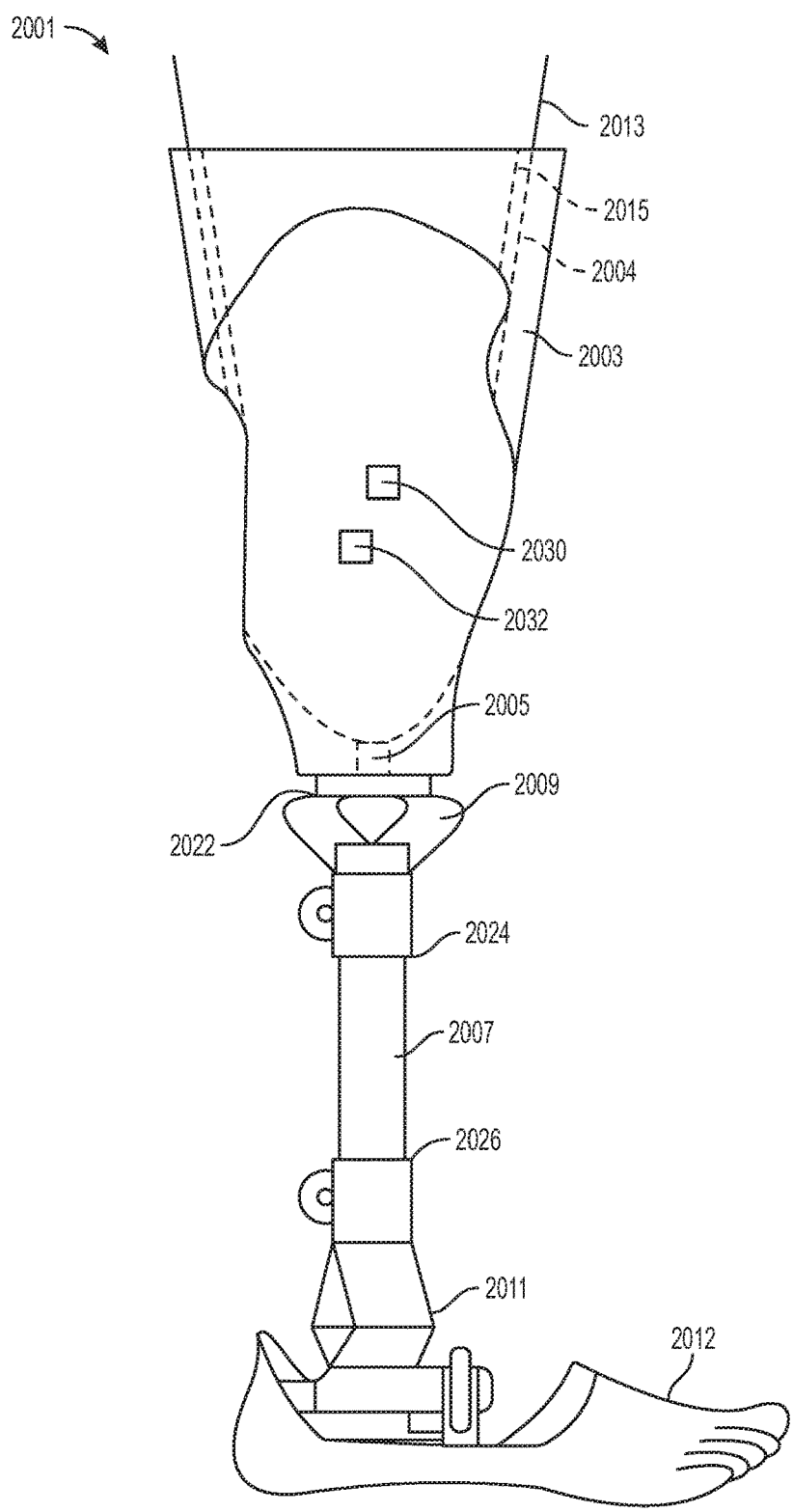
FIG. 11 is a side view of a biomechanical device with portions shown in phantom according to still another embodiment of the invention.
Figure 12:
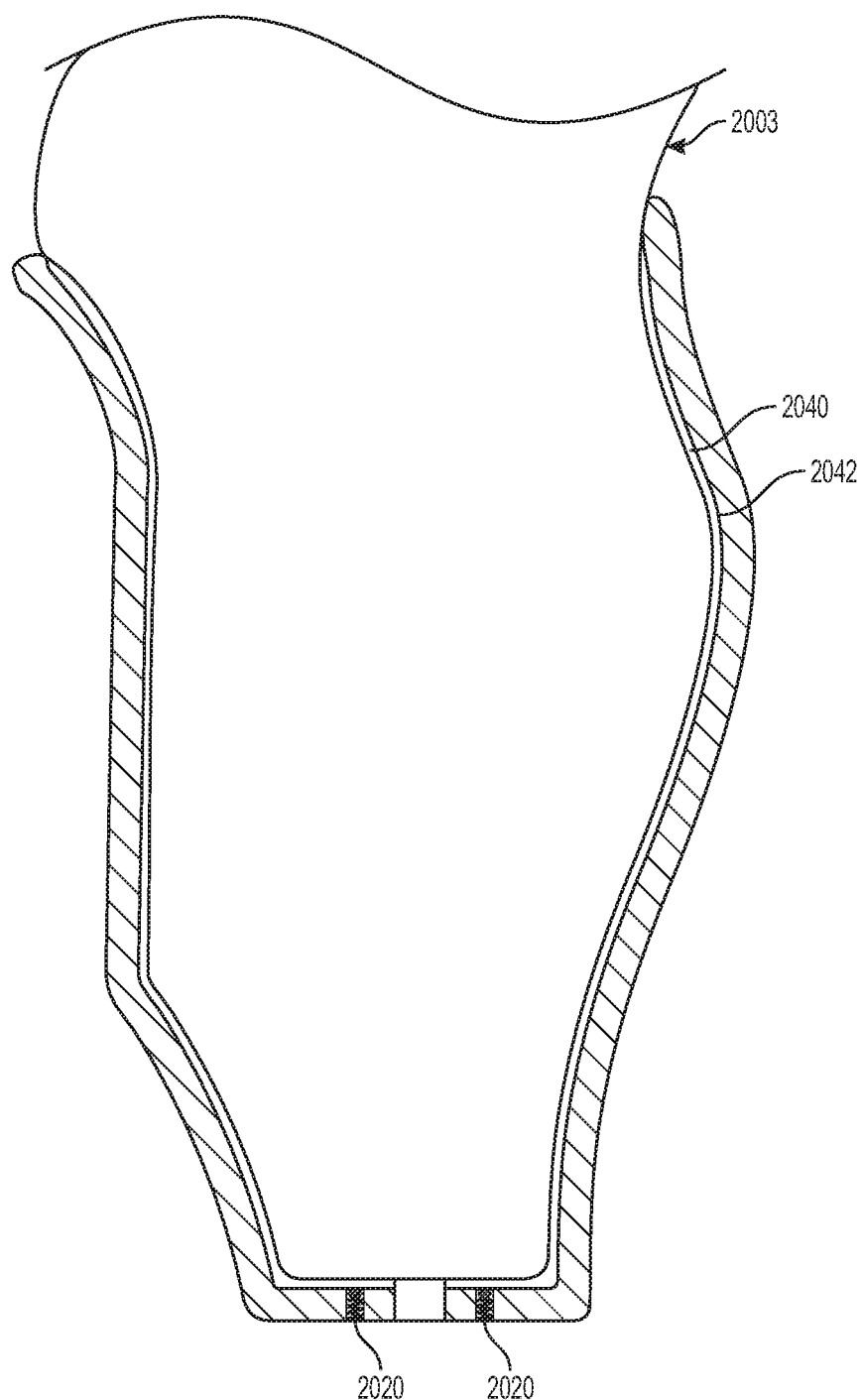
FIG. 12 is a cross section view of a socket of the biomechanical device of FIG. 11.

FIGS. 11-12 illustrate an embodiment having damping apparatus 2020 incorporated into use with transtibial prosthetic 2001 (although other prosthetics are within the scope of the disclosure). The transtibial prosthetic 2001 may include a socket 2003, a sock 2004 and pin 2005, a pylon 2007, an adjustment pyramid 2009, a rotational ankle 2011, and a foot 2012. The socket 2003 is carefully molded to a user's limb 2013. The limb 2013 is covered with an elastic sock 2015 to compress the residual limb and to aid in avoiding edema. Situated over the elastic sock 2015 is the sock 2004 (which may be, for example, silicon or fabric) with the pin 2005 attached thereto. The fit of the socket 2003 is important as it can cause discomfort or tissue damage. As the residual limb 2013 is likely to change shape and size over time, additional sock(s) having varying thicknesses may be added atop the silicon sock 2004 to account for this change or to aid in the initial fit of the socket 2003. In some cases, a leather pad may further be added to aid in the fit of the limb 2013 to the socket 2003.

The pin 2005 is engaged with the adjustment pyramid 2009 and locked into position. The pyramid 2009 is affixed to the socket 2003 at a first end 2022 and to the pylon 2007 at a second end 2024. At a distal end 2026 of the pylon 2007 is the rotational ankle 2011 that is further attached to the foot 2012.

Damping apparatus 2020 (FIG. 12) may be provided at the interface between the prosthetic 2001 and the patient's limb 2013. The damping apparatus 2020 may be configured as any of the damping apparatus described herein, including the damping apparatus 71 (indicated by reference number 2020). Likewise, damping apparatus 2040 may be the damping compositions, such as adhesives and/or coatings incorporating 3D structures (e.g., 3D structure 200 shown in FIG. 9) for reducing forces as discussed above. In one embodiment, a surface 2042 of the prosthetic 2001 that interfaces with the patient's appendage is coated in a composition 2040 such as a gel incorporating 3D structure for reducing impact forces.

Similar to the embodiments described above, the prosthetic 2001 or any of the layering socks 2004, 2015, 2017 may be equipped with sensors 2030 and/or processors 2032 for influencing the response of the composition 2040 (or the apparatus 2020, as the case may be). The sensors 2030 and processors 2032 may function substantially similarly to sensors 802 and processors 804 described above. Further, it shall be understood by those of skill in the art that the damping apparatus 2020 and/or 2040 may be magnetically or electrically responsive, and that the prosthetic 2001 may therefore be equipped (e.g., in the prosthetic 2001 itself, or via a wrap or sock 2004, 2015, 2017) with magnets or other means for providing electrical stimulation as described herein in order to effectuate the controlled response of the damping apparatus 2020 and/or 2040.

In still another embodiment, sensors may be provided throughout the body for detecting stimulation, which may be used to communicate with a biomechanical device implanted into or onto the body. For example, sensors may be implanted at or near a nerve, or another joint. The sensor may be, for example, a proximity or motion sensors which may be placed at or near a joint in the body for detecting movement of the joint. Alternately, the sensor may be configured to sense electrochemical changes in the body, for example, near a nerve. The sensors may sense movement or electrochemical changes and provide signals to another part of the body. In one example, electrochemical sensors may be placed at or near a nerve which has been severed in a patient which prevents a signal from reaching a patient's joint (e.g., a knee). The joint may be replaced with a motorized joint configured to receiving signals from the electrochemical sensors. When the patient wants to walk, the electrochemical sensors sense the electrical impulse in the nerve and send a signal to the motor to effectuate movement of the joint. The electrochemical sensor may thus act to "complete the circuit" to allow the patient to walk even with a severed nerve.

In another example, motion sensors may be placed at or near a working joint (e.g., the right knee). A non-working joint (e.g., the left knee) may be replaced with a motorized joint configured to receive signals from the motion sensors. When the motion sensors detect movement of the working joint (e.g., the right knee) the sensors may send a signal to the mechanical joint (e.g., the left knee) initiating movement and allowing a patient to walk. It shall be understood that the motion sensors may be placed near joints that are not directly related to the non-working joint. For example, if a patient can move his or her arm, the sensors may be placed at or near his or her arms to effectuate movement of a knee, ankle, or other joint.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention. Further, it will be understood that certain features and subcombinations may be of utility and may be employed within the scope of the disclosure. Further, various steps set forth herein may be carried out in orders that differ from those set forth herein without departing from the scope of the present methods. This description shall not be restricted to the above embodiments.

It is to be understood that while certain forms of the present invention have been illustrated and described herein, it is not to be limited to the specific forms or arrangement of parts described and shown.

What is claimed is:

1. A joint implant, comprising a bone implantable component; and a bearing component having an articulation surface that is sized and shaped to substantially mate with at least a portion of the bone implantable component, the articulation surface having a damping adhesive, the damping adhesive including a plurality of three-dimensional particles dispersed therein, the particles being physically displaced in response to an applied force; wherein the damping adhesive is disposed on an inferior surface of the bearing component, and a second bone implantable component is adhered to the bearing component by means of the damping adhesive.

2. The joint implant of claim 1, wherein the applied force is one of a magnetic field, an electric field, a subsonic field, an ultrasonic field, and an electromagnetic field.

3. The joint implant of claim 1, further comprising a sensor for measuring an amplitude and frequency spectrum of a movement force upon the joint implant caused by movement thereof;
   wherein, in a use configuration: the applied force is dependent on the amplitude and frequency spectrum of the movement force.

4. The joint implant of claim 3, further comprising a force generating device, and wherein the applied force is one of a magnetic field and an electric field.

5. A joint implant, comprising:
   a bone implantable component;
   a bearing component having an articulation surface that is sized and shaped to substantially mate with at least a portion of the bone implantable component, the articulation surface having an adhesive, the adhesive including a plurality of three-dimensional particles dispersed therein, the particles being physically displaced in response to an applied force;
   a sensor for measuring an amplitude and frequency spectrum of a movement force upon the joint implant caused by movement thereof; and
   a force generating device;
   wherein:
      the applied force is one of a magnetic field and an electric field;
      in a use configuration the applied force is dependent on the amplitude and frequency spectrum of the movement force; and
      the sensor senses the movement force in real-time, thus sending a substantially continuous signal to the force generating device, and wherein the applied force is adjusted based on the signal.

6. A joint implant, comprising:
   a bone implantable component;
   a bearing component having an articulation surface that is sized and shaped to substantially mate with at least a portion of the bone implantable component, the articulation surface having an adhesive, the adhesive including a plurality of three-dimensional particles dispersed therein, the particles being physically displaced in response to an applied force
   a sensor for measuring an amplitude and frequency spectrum of a movement force upon the joint implant caused by movement thereof; and
   a force generating device,
   wherein:
   in a use configuration: the applied force is dependent on the amplitude and frequency spectrum of the movement force;
   the applied force is one of a magnetic field and an electric field; and
   the force generating device and sensor are situated within at least one of a joint wrap, a bracelet, anklet, a cellular phone, and a watch.

7. A joint implant, comprising:
   a bone implantable component;
   a bearing component having an articulation surface that is sized and shaped to substantially mate with at least a portion of the bone implantable component, the articulation surface having an adhesive, the adhesive including a plurality of three-dimensional particles dispersed therein, the particles being physically displaced in response to an applied force a sensor for measuring an amplitude and frequency spectrum of a movement force upon the joint implant caused by movement thereof; and a force generating device, wherein:

in a use configuration: the applied force is dependent on the amplitude and frequency spectrum of the movement force;

the applied force is one of a magnetic field and an electric field; and the sensor sends a signal to the force generating device, the signal initiating the particles being physically displaced.

8. A joint implant, comprising:

a bone implantable component;

a bearing component having an articulation surface that is sized and shaped to substantially mate with at least a portion of the bone implantable component, the articulation surface having an adhesive, the adhesive including a plurality of three-dimensional particles dispersed therein, the particles being physically displaced in response to an applied force; and a sensor for measuring an amplitude and frequency spectrum of a movement force upon the joint implant caused by movement thereof;

wherein in a use configuration: the applied force is dependent on the amplitude and frequency spectrum of the movement force; and the physical displacement of the particles is at controlled time intervals, the physical displacement causing an opposing force having a spread spectrum inverse waveform from the movement force.

9. A joint implant system, comprising:

a force generating device;

a joint implant having:

a bone implantable component; and a bearing component having an articulation surface that is sized and shaped to substantially mate with at least a portion of the bone implantable component, the articulation surface having an adhesive, the adhesive including a plurality of three-dimensional particles dispersed therein, the particles being physically displaced in response to an applied force generated by the force generated device; and a sensor measuring an amplitude and frequency spectrum of a movement force upon the joint implant caused by movement of the joint implant.

10. The joint implant system of claim 9, further comprising a wrap, and wherein at least one item selected from the group consisting of the force generating device and the sensor is coupled to the wrap.

11. The joint implant system of claim 9, wherein the sensor detects the movement force in real-time, and sends a substantially continuous signal to the force generating device, and wherein the applied force is adjusted based on the signal.

12. The joint implant of claim 9, wherein the wrap is at least one of a joint wrap, a bracelet, anklet, a cellular phone, and a watch.

13. The joint implant of claim 9, wherein the applied force is one of a magnetic field, an electric field, a subsonic field, an ultrasonic field, and an electromagnetic field.

14. The joint implant of claim 9, wherein the sensor sends a signal to the force generating device, the signal initiating the particles being physically displaced.

15. The joint implant of claim 9, wherein the physical displacement of the particles is at controlled time intervals, the physical displacement causing an opposing force having a spread spectrum inverse waveform from the movement force.

16. The joint implant of claim 9, wherein the movement force received by the joint implant causes the particle to compress from a natural expanded state to a compressed state, the particle subsequently returning to its expanded state, therein imparting an opposing force on the bearing component which is less than an initial force received by the bearing component.

17. The joint implant of claim 9, wherein an inferior surface of the bearing component is connected to a second bone implantable component by means of the adhesive.

18. The joint implant of claim 9, wherein the joint implant is attached at least one of the following: shoulder, knee, hip, wrist, ankle, temporomandibular, and elbow.

19. A joint implant, comprising:

a bone implantable component;

a bearing component having an articulation surface that is sized and shaped to substantially mate with at least a portion of the bone implantable component, the articulation surface having a composition with a plurality of three-dimensional particles dispersed therein, the particles being physically displaced in response to an applied force; and a sensor for measuring an amplitude and frequency spectrum of a movement force upon the joint implant caused by movement thereof;

wherein the plurality of three-dimensional particles includes at least one item selected from the group consisting of:

a) a plurality of layered graphene particles;
b) a plurality of graphene nanotube particles;
c) a plurality of dendrimer particles;
d) a plurality of fullerene particles; and
e) a plurality of C60 particles; and wherein, in a use configuration, the applied force is dependent on the amplitude and frequency spectrum of the movement force.

20. The joint implant of claim 19, further comprising a force generating device, and wherein the applied force is one of a magnetic field and an electric field.

21. The joint implant of claim 19, wherein the sensor senses the movement force in real-time, thus sending a substantially continuous signal to the force generating device, and wherein the applied force is adjusted based on the signal.

22. The joint implant of claim 19, wherein the force generating device and sensor are situated within at least one of a joint wrap, a bracelet, anklet, a cellular phone, and a watch.

23. The joint implant of claim 19, wherein the sensor sends a signal to the force generating device, the signal initiating the particles being physically displaced.

24. The joint implant of claim 19, wherein the physical displacement of the particles is at controlled time intervals, the physical displacement causing an opposing force having a spread spectrum inverse waveform from the movement force.

* * * * *